United States Patent [19]
Wright, Jr. et al.

[11] Patent Number: 6,015,713
[45] Date of Patent: Jan. 18, 2000

[54] TRANSGENIC FISH AND A METHOD OF HARVESTING ISLET CELLS THEREFROM

[75] Inventors: James R. Wright, Jr., Halifax; Bill Pohajdak, Dartmouth, both of Canada

[73] Assignee: Dalhousie University, Nova Scotia, Canada

[21] Appl. No.: 08/750,391

[22] PCT Filed: Mar. 22, 1996

[86] PCT No.: PCT/CA96/00171

§ 371 Date: Dec. 6, 1996

§ 102(e) Date: Dec. 6, 1996

[87] PCT Pub. No.: WO96/32087

PCT Pub. Date: Oct. 17, 1996

[30]     Foreign Application Priority Data

Apr. 6, 1995  [US]  U.S. .................................. 08/417866

[51] Int. Cl.[7] ............................. C12N 15/00; C12N 5/00; A01K 67/00
[52] U.S. Cl. ........................... 435/378; 435/325; 800/20; 800/21
[58] Field of Search ................................ 424/93.1, 93.21; 514/44; 800/2, DIG. 1–4; 530/350; 435/320.1, 325, 378

[56]              References Cited

U.S. PATENT DOCUMENTS 5,476,779  12/1995  Chen et al. .......................... 435/240.1
5,545,808   8/1996  Hew et al. .................................. 800/2

FOREIGN PATENT DOCUMENTS 0 179 576    9/1985  European Pat. Off. ........ C12P 21/00
3545237 A1   6/1987  Germany ....................... A61M 37/00

OTHER PUBLICATIONS

Rokkones et al. Microinjection and expression of a mouse metallothionein human growth hormone fusion gene in fertilized salmonid eggs. J. Comp. Physiol. B, vol. 158, pp. 751–758, 1989.

Tiedge et al. Gene therapy of diabetes mellitus–aims, methods, and future prospects. Exp. and Clin. Biochem., vol. 103/suppl. 2, pp. 46–55, May 1995.

Noel et al. Prospects for genetic manipulation in diabetes. Diabetes Annual, vol. 10, pp. 65–84, 1996.

Chen et al. Trangenic fish: Ideal models for basic research and biotechnological applications. Zoological Studies, vol. 34, No. 4, pp. 215–234, Oct. 1995.

Chan et al. "Insulin and insulin–like growth factor genes in fishes and other primitive chordates" *Biochemistry and molecular Biolocy of Fishes*, 2, Hochachka P. and Mommesen T. (eds.) Amsterdam: Elsevier, 1993, pp. 407–17.

Furuchi et al. "A Radioimmunoassay Method for Determination of Fish Plasma Insulin" *Bull Jap Soc. Sci Fish* 46:1177–1181 (1980).

Gerber and Hare, "GABA in Peripheral Tissues: Presence and Actions in Endocrine Pancreatic Function" *Brain Research Bulletin* 5(Supp. 2):341–346 (1980).

Hobart et al. "Comparison of the nucleic acid sequence of anglerfish and mammalian insulin mRNA's from cloned CDNA's" *Science* 210: 1360–1363 (1980).

Iwata et al., "Feasibility of agarose microbeads with xenogeneic islets as a bioartificial pancreas" *Journal of Biomedical Materials Research* 28: 1003–1011 (1994).

Iwata et al., "Strategy for developing microbeads applicable to islet xenotransplantation into a spontaneous diabetic NOD mouse" *Journal of Biomedical Materials Research* 28: 1201–1207 (1994).

Kelly et al., "Experimental Diabetes Mellitus in a Teleost Fish. II. Roles of Insulin, Growth Hormone (GH), Insulin–Like Growth Factor–I, and Hepatic GH Receptors in Diabetic Growth Inhibition in the Goby, *Gillichthys mairabilis*" *Endocrinology* 132(6): 2696–2702 (1993).

Lanza et al., "A Simple Method for Transplanting Discordant Islets into Rats Using Alginate Gel Spheres" *Transplantation* 59:1485–9 (1995).

Mommesen and Plisetskaya, "Insulin in Fishes and Agnathans: History, Structure, and Metabolic Regulation" *Rev. Aquacic Sci.* 4:225–59 (1991).

Nguyen et al., "Characterization of the pancreatic hormones from the Brockmann body of the tilapia—implications for islet xenograft studies" *Comp. Biochem. and Physiol* IIIC(1): 33–44 (1995).

Patent and Foa, "Radioimmunoassay of Insulin in Fishes: Experiments in Vivo and in Vitro" *Gen Comp Endocrinol* 16:41–6 (1971).

Penman et al. "Factors affecting survival and integration following microinjection of novel DNA into rainbow trout eggs" *Aquaculture* 85: 35–50 (1990).

Pipeleers et al. "Glucose–induced insulin release depends on functional cooperation between islet cells" *Proc. Natl. Acad. Sci.* (*USA*) 79: 7322–7325 (1982).

Rahman and Maclean, "Production of transgenic tilapia (*Oreochromis niloticus*) by one–cell–stage microinjection" *Aquaculture* 105: 219–32 (1992).

(List continued on next page.)

*Primary Examiner*—Bruce R. Campell
*Assistant Examiner*—Deborah J. R. Clark
*Attorney, Agent, or Firm*—Gray Cary Ware & Freidenrich; Stephen E. Reiter

[57]              ABSTRACT

This invention relates to transgenic fish containing a humanized insulin gene which has been altered to secrete human insulin and its use in the treatment of diabetes. In the transgenic fish of the present invention, the fish insulin gene has been modified to code for human insulin gene while leaving the regulatory sequences of fish insulin gene intact. Islet transplantation may provide the meticulous glycemia control required in the treatment of diabetes. The islet tissue of the present invention offers an inexpensive and a nearly unlimited supply of human insulin-producing tissue and therefore, may be useful in the treatment of diabetes. In this regard, an improved method of mass isolation of islet tissue is provided by the present invention. The present invention also provides the use of the humanized insulin gene to promote growth in fish.

2 Claims, 4 Drawing Sheets

OTHER PUBLICATIONS

Saiki et al., "Primer–Directed Enzymatic Amplification of DNA with a Thermostable DNA Polymerase" *Science* 239: 487–491 (1988).

Schrezenmeir et al., "Effect of Microencapsulation on Oxygen Distribution in Islets Organs" *Transplantation* 57: 1308–1314 (1994).

Schrezenmeir et al., "Long–Term Function of Single–Cell Preparations of Piscine Principal Islets in Hollow Fibers" *Transplant Proc.* 24:2941–2945 (1992).

Steiner et al. "Structure and Evolution of the Insulin Gene" *Ann. Rev. Genet.* 19:463–484 (1985).

Thorpe and Ince, "Plasma insulin levels in teleosts determined by a charcoal–separation radioimmunoassay technique" *Gen Comp Endocrinol* 30:332–339 1976.

Tilzey et al. "The development of a homologous teleost insulin radioimmunoassay and its use in the study of adrenaline on insulin secretion from isolated pancreatic islet tissue of the rainbow trout. *Salmo gairdnerii* (R.)" *Comp Biochem Physiol.* 81A:821–825 (1985).

Uraiwan and Doyle, "Replicate variance and the choice of selection procedure for tilapia (*Oreochromis nilotic*) stock improvement in Thailand" *Aquaculture* 57: 93–98 (1986).

Wright et al., "Longterm Function of the Teleost Fish Principal Islets (Brockmann bodies) After Transplantation Under the Renal Capsule in Diabetic Nude Mice" *Transplant Proc.* 24:3029–3030 (1992).

Wright et al., "Experimental Xenotransplantation Using Principal Islets of Teleost Fish (Brockmann Bodies): Graft Survival in Selected Strains of Inbred Mice" *Transplant Proc.* 26:770 (1994).

Wright et al., "Experimental Transplantation With Principal Islets of Teleost Fish (Brockmann Bodies): Long–Term Function of Tilapia Islet Tissue in Diabetic Nude Mice" *Diabetes* 41:1528–32 (1992).

Yang and Wright, "A Method for Mass Harvesting Islets (Brockmann Bodies) From Teleost Fish" *Cell transplant.* 4:621–628 (1995).

Yang et al, "Long–Term Function of Fish Islet Xenografts in Mice by Alginate Encapsulation" *Transplantation* 64:28–32 (1997).

Insulin A-Chain

Gly-Ile-Val-Glu-Glu-Cys-Cys-His-Lys-Pro$^{10}$-Cys-Thr-Ile-Phe-Asp-Leu-Gln-Asn-Tyr-Cys$^{20}$-Asn

Insulin B-Chain

Val-Gly-Gly-Pro-Gln-His-Leu-Cys-Gly-Ser$^{10}$-His-Leu-Val-Asp-Ala-Leu-Tyr-Leu-Val-Cys$^{20}$-Gly-Asp-Arg-Gly-Phe-Phe-Tyr-Asn-Pro-Arg$^{30}$

FIG. 1

Insulin A-Chain

| Tilapia | GIVEE | CCHKP | CTIFD | LQNYC | N |
|---|---|---|---|---|---|
| Human | ----Q | --TSI | -SLYQ | -E--- | - |

Insulin B-Chain

| Tilapia | VGGPQ | HLCGS | HLVDA | LYLVC | GDRGF | FYNPR |
|---|---|---|---|---|---|---|
| Human | FVN- | ----- | ---E- | ----- | -E--- | --T-K T |

FIG. 2

```
                                             ....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTGTGTT
```

CAGCTCTTTTCCAGC ATG GCA GCG CTC TGG CTC CAG GCC TTC TCC CTG CTC GTC TTA ATG ATG
                met ala ala leu trp leu gln ala phe ser leu leu val leu met met GTT TCG TGG CCG GGC TCC CAG GCC GTC GGT GGG CCA CAG CAC CTG TGC GGC TCC CAC CTG
val ser trp pro gly ser gln ala val gly gly pro gln his leu cys gly ser his leu GTG GAT GCC CTG TAC CTG GTC TGT GGG GAC AGA GGC TTC TTC TAC AAC CCC AGG AGA GAT
val asp ala leu tyr leu val cys gly asp arg gly phe phe tyr asn pro arg arg asp GTG GAC CCT CTG CTT GGT GAGACCACCAACCACAAACAGAAACACTAGACAAACTATTTGAGGGCAGCTTTTC
val asp pro leu leu

TTTCTCTGAGTTCACTTTAAATCAGCTTTCATGTTGGAAACATGGTAATAGTAATTTTCCATATCTTTATGGACCCTAC

ATGATTAGTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG   GT TTC CTC CCT CCA AAG GCA GGT GGT GCT GTG GTG CAA GGT
                            gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG GAA TGC TGT CAC AAA CCC TGT ACC ATC TTC GAC CTG CAG AAC TAC TGC AAC TGA ACT
glu glu cys cys his lys pro cys thr ile phe asp leu gln asn tyr cys asn *

```
GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAAATTATCAAATTGAATTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA
```

FIG. 3

```
                                                                  ....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTGTGTT

CAGCTCTTTTCCAGC ATG GCA GCG CTC TGG CTC CAG GCC TTC TCC CTG CTC GTC TTA ATG ATG
                met ala ala leu trp leu gln ala phe ser leu leu val leu met met GTT TCG TGG CCG GGC TCC CAG GCC TTC GTG CAG CAG CAC CTG TGC GGA TCC CAC CTG GTG
val ser trp pro gly ser gln ala PHE VAL ASN gln his leu cys gly ser his leu val GAG GCC CTG TAC CTG GTC TGT GGG GAG AGA GGC TTC TTC TAC ACC CCC AAG AGA GAT GTG
GLU ala leu tyr leu val cys gly GLU arg gly phe phe tyr THR pro LYS arg asp val GAC CCT CTG CTT G        GTGAGACCACCAACCACAAACAGAAACACTAGACAAACTATTTGAGGGCAGCTTTTC
asp pro leu leu

TTTCTCTGAGTTCACTTTAAATCAGCTTTCATGTTGGAAACATGGTAATAGTAATTTTTCCATATCTTTATGGACCCTAC

ATGATTAGTTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG   GT TTC CTC CCT CCA AAG GCA GGT GGT GCT GTG GTG CAA GGT
                         gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG CAA TGC TGT ACC TCC ATT TGT TCC CTG TAC CAG CTG GAG AAC TAC TGC AAC TGA ACT
glu GLN cys cys THR SER ILE cys SER LEU TYR GLN leu GLU asn tyr cys asn *

GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAATTATCAAATTGAATTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA
```

FIG. 4

....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTGTGTT

CAGCTCTTTTCCAGC ATG GCA GCG CTC TGG CTC CAG GCC TTC TCC CTG CTC GTC TTA ATG ATG
       met ala ala leu trp leu gln ala phe ser leu leu val leu met met GTT TCG TGG CCG GGC TCC CAG GCC TTC GTG CAG CAG CAC CTG TGC GGA TCC CAC CTG GTG
val ser trp pro gly ser gln ala PHE VAL ASN gln his leu cys gly ser his leu val GAG GCC CTG TAC CTG GTC TGT GGG GAG AGA GGC TTC TTC TAC ACC CCC AAG ACC AGA GAT
GLU ala leu tyr leu val cys gly GLU arg gly phe phe tyr THR pro LYS THR arg asp GTG GAC CCT CTG CTT G GTGAGACCACCAACCACAAACAGAAACACTAGACAAACTATTTGAGGGCAGCTTTTC
val asp pro leu leu

TTTCTCTGAGTTCACTTTAAATCAGCTTTCATGTTGGAAACATGGTAATAGTAATTTTCCATATCTTTATGGACCCTAC

ATGATTAGTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG GT TTC CTC CCT CCA AAG GCA GGT GGT GCT GTG GTG CAA GGT
         gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG CAA TGC TGT ACC TCC ATT TGT TCC CTG TAC CAG CTG GAG AAC TAC TGC AAC TGA ACT
glu GLN cys cys THR SER ILE cys SER LEU TYR GLN leu GLU asn tyr cys asn *

GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAATTATCAAATTGAATTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA

FIG. 5

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 21 amino acids
       (B) TYPE: amino acid
       (C) STRANDEDNESS: single
       (D) TOPOLOGY: linear (ii) MOLECULE TYPE: peptide (v) FRAGMENT TYPE: N-terminal (vi) ORIGINAL SOURCE:
       (A) ORGANISM: TILAPIA INSULIN A CHAIN (xi) SEQUENCE DESCRIPTION: SEQ ID NO:1:

Gly Ile Val Glu Glu Cys Cys His Lys Pro Cys Thr Ile Phe Asp Leu
1               5                   10                  15

Gln Asn Tyr Cys Asn
            20

(2) INFORMATION FOR SEQ ID NO:2:

(i) SEQUENCE CHARACTERISTICS:
       (A) LENGTH: 30 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: TILAPIA INSULIN B CHAIN (xi) SEQUENCE DESCRIPTION: SEQ ID NO:2:

Val Gly Gly Pro Gln His Leu Cys Gly Ser His Leu Val Asp Ala Leu
1               5                   10                  15

Tyr Leu Val Cys Gly Asp Arg Gly Phe Phe Tyr Asn Pro Arg
            20                  25                  30

(2) INFORMATION FOR SEQ ID NO:3:

(i) SEQUENCE CHARACTERISTICS:
       (A) LENGTH: 21 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: HUMAN INSULIN A CHAIN (xi) SEQUENCE DESCRIPTION: SEQ ID NO:3:

Gly Ile Val Glu Gln Cys Cys Thr Ser Ile Cys Ser Leu Tyr Gln Leu
1               5                   10                  15

Glu Asn Tyr Cys Asn
            20

(2) INFORMATION FOR SEQ ID NO:4:

(i) SEQUENCE CHARACTERISTICS:
       (A) LENGTH: 30 amino acids (B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN INSULIN B CHAIN (xi) SEQUENCE DESCRIPTION: SEQ ID NO:4:

```
Phe Val Asn Gln His Leu Cys Gly Ser His Leu Val Glu Ala Leu Tyr
1               5                  10                  15
Leu Val Cys Gly Glu Arg Gly Phe Phe Tyr Thr Pro Lys Thr
            20                  25                  30
```

(2) INFORMATION FOR SEQ ID NO:5:

(i) SEQUENCE CHARACTERISTICS:
(A) LENGTH: 2078 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: TILAPIA INSULIN GENE (xi) SEQUENCE DESCRIPTION: SEQ ID NO:5:

| | | | | | |
|---|---|---|---|---|---|
| GTCCCCATAA | TCGCACACAA | GTCCCCACAA | TGTAGGTGAA | ATAGGTTCCA | CGGAAACACG | 60 |
| TGGAACAGGG | GGTGTGTCCA | GGTGGTGCTG | GTGGAGTATA | AATGGAGAGA | AGGCTCTTGG | 120 |
| TTCTGCCTCA | CACAGAAAAG | CTGCTCCTGC | CCTTCATCTC | AGAGTTACCT | CCTCCTCTCT | 180 |
| GTCTGTGCAG | GTGAGTGCTG | GCTGTAGGTT | TGGTTGTGAG | GACAGTGACT | GTGATGCTAA | 240 |
| CGTGAATGTG | CTTTTGTGTT | CAGCTCTTTT | CCAGCATGGC | AGCGCTCTGG | CTCCAGGCCT | 300 |
| TCTCCCTGCT | CGTCTTAATG | ATGGTTTCGT | GGCCGGGCTC | CCAGGCCGTC | GGTGGGCCAC | 360 |
| AGCACCTGTG | CGGCTCCCAC | CTGGTGGATG | CCCTGTACCT | GGTCTGTGGG | GACAGAGGCT | 420 |
| TCTTCTACAA | CCCCAGGAGA | GATGTGGACC | CTCTGCTTGG | TGAGACCACC | AACCACAAAC | 480 |
| AGAAACACTA | GACAAACTAT | TTGAGGGCAG | CTTTTCTTTC | TCTGAGTTCA | CTTTAAATCA | 540 |
| GCTTTCATGT | TGGAAACATG | GTAATAGTAA | TTTTCCATAT | CTTTATGGAC | CCTACATGAT | 600 |
| TAGTTTACAT | CTATTGCCAT | TTGTCTCAAC | ACCTGCATCA | TATAATAGCG | CTGATTTTGT | 660 |
| AACACTTTGT | GTTAGAATTA | GTAATTTATG | TTCTAATAAT | GTTTGATATG | TATTCTTTAA | 720 |
| TATAAATGAC | CAGAATTTTT | AGATCTGAAC | ATTCACCTGC | TCTTCATCCC | ATCAGGTTTC | 780 |
| CTCCCTCCAA | AGGCAGGTGG | TGCTGTGGTG | CAAGGTGGTG | AGAATGAAGT | GACCTTCAAA | 840 |
| GACCAGATGG | AAATGATGGT | GAAGCGAGGC | ATTGTGGAGG | AATGCTGTCA | CAAACCCTGT | 900 |
| ACCATCTTCG | ACCTGCAGAA | CTACTGCAAC | TGAACTGCTC | TGCTGGACTT | TGTTTAGTCG | 960 |
| AGCCAGGCTC | GGCTATTCAG | GTCTGAGTCC | CAGCCCCACC | TCGCTCCCTG | CTTCAGAGGA | 1020 |
| GAGCCACAGC | TGTCCTCTCT | CTGAAAACCA | ACTGCTGTCA | AATGAAGTGC | TGAGAAATGG | 1080 |
| ATAAAATTAA | TTTTCCAAGA | AATAAAAATG | CAAAATGTGA | CAACGTGAGG | CAAAAAAGTG | 1140 |
| TGTTCTTTTG | TTGTGATGAA | TTCAGTTAAT | TGATTAAAGT | GAAAACTCGA | ACATGTTAGG | 1200 |
| TACCTGCTGC | TATCCAGCAC | AAACTGCTGA | GCTTTCACTT | TCCAAAGCTT | TGTGTTTAGC | 1260 |
| TTATAGTGTC | TCTGAACAGG | ATATAAACAC | ATCATGCACT | CTGACATGAT | GTCCTTTTCA | 1320 |
| AACAATCCCT | TGTCATCTTC | ATTTCAGCAG | GTCAGTGTTT | TTTATTCAGG | TCCTCGTGAT | 1380 |
| GACACAGAAG | ATAAAAACAC | CAAGTATTCT | AAAAATTATC | AAATTGAATT | TTAAGTTCAA | 1440 |

-continued

```
AAGCATTCTT CCATCACAGT CAACAGAACC CCAAGACCTG AAGTTCCAAA GGCCTGTGGT      1500

GTTACCACTA TGCTATCTAC ATATGTTACC TGCTTTTAAC TATTAAACGG AGCAGATGGA      1560

TCAGAAGGTT AATAGCTGAT CAGATCATGT CAGCTCATTA GCTTCAGTTT GTTTTACTGA      1620

GTGCTGTAAC CACTCAATCA GAAACACACT GTTACTTAAT CTGAGTACAT ACTTGTATAC      1680

ATTAAACTTG GAAAAAGATA GATGTGAAAT GTAAAAGTGA GGTCAATCGT CAAATGTGAC      1740

ACGATATTTG GATCTGTTTA TCCTTCCAGG ATCACGGGGC GGGGAGAGCC TATCCCAGCT      1800

ACCATAGTGC GAGAGGTCAG GTACACCCTG GAGAGGTCAA CAGCCTGTCA CAGGGTTTAC      1860

GCTCAGAGAC AAGCAACCAC GCCACTTCGG CTTATACCAG TATTATTTCC TAAATGTTGC      1920

CAATAAAAAA CAAAATCAGT AGAATTTTAA GCAGTTTTCA TTTTAATTTA ACCTCATTTG      1980

AAGAAGAAGT CAGAGGTCCA AAGTATGGGA ATATTTATAA TTCCAATGTT GTCAATTCAA      2040

ATAATGGCAA TAAGAAACAT AGTTTGAAAT AGAATAAG                              2078
```

(2) INFORMATION FOR SEQ ID NO:6:

(i) SEQUENCE CHARACTERISTICS:
        (A) LENGTH: 2072 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: HUMANIZED TILAPIA INSULIN NO:1

(xi) SEQUENCE DESCRIPTION: SEQ ID NO:6:

```
GTCCCCATAA TCGCACACAA GTCCCCACAA TGTAGGTGAA ATAGGTTCCA CGGAAACACG        60

TGGAACAGGG GGTGTGTCCA GGTGGTGCTG GTGGAGTATA AATGGAGAGA AGGCTCTTGG       120

TTCTGCCTCA CACAGAAAAG CTGCTCCTGC CCTTCATCTC AGAGTTACCT CCTCCTCTCT       180

GTCTGTGCAG GTGAGTGCTG GCTGTAGGTT TGGTTGTGAG GACAGTGACT GTGATGCTAA       240

CGTGAATGTG CTTTTGTGTT CAGCTCTTTT CCAGCATGGC AGCGCTCTGG CTCCAGGCCT       300

TCTCCCTGCT CGTCTTAATG ATGGTTTCGT GGCCGGGCTC CCAGGCCTTC GTGCAGCAGC       360

ACCTGTGCGG ATCCCACCTG GTGGAGGCCC TGTACCTGGT CTGTGGGGAG AGAGGCTTCT       420

TCTACACCCC CAAGAGAGAT GTGGACCCTC TGCTTGGTGA GACCACCAAC CACAAACAGA       480

AACACTAGAC AAACTATTTG AGGGCAGCTT TTCTTTCTCT GAGTTCACTT TAAATCAGCT       540

TTCATGTTGG AAACATGGTA ATAGTAATTT TCCATATCTT TATGGACCCT ACATGATTAG       600

TTTACATCTA TTGCCATTTG TCTCAACACC TGCATCATAT AATAGCGCTG ATTTTGTAAC       660

ACTTTGTGTT AGAATTAGTA ATTTATGTTC TAATAATGTT TGATATGTAT TCTTTAATAT       720

AAATGACCAG AATTTTTAGA TCTGAACATT CACCTGCTCT TCATCCCATC AGGTTTCCTC       780

CCTCCAAAGG CAGGTGGTGC TGTGGTGCAA GGTGGTGAGA ATGAAGTGAC CTTCAAAGAC       840

CAGATGGAAA TGATGGTGAA GCGAGGCATT GTGGAGCAAT GCTGTACCTC CATTTGTTCC       900

CTGTACCAGC TGGAGAACTA CTGCAACTGA ACTGCTCTGC TGGACTTTGT TTAGTCGAGC       960

CAGGCTCGGC TATTCAGGTC TGAGTCCCAG CCCCACCTCG CTCCCTGCTT CAGAGGAGAG      1020

CCACAGCTGT CCTCTCTCTG AAAACCAACT GCTGTCAAAT GAAGTGCTGA GAAATGGATA      1080

AAATTAATTT TCCAAGAAAT AAAAATGCAA AATGTGACAA CGTGAGGCAA AAAAGTGTGT      1140

TCTTTTGTTG TGATGAATTC AGTTAATTGA TTAAAGTGAA AACTCGAACA TGTTAGGTAC      1200

CTGCTGCTAT CCAGCACAAA CTGCTGAGCT TTCACTTTCC AAAGCTTTGT GTTTAGCTTA      1260
```

-continued

```
TAGTGTCTCT GAACAGGATA TAAACACATC ATGCACTCTG ACATGATGTC CTTTTCAAAC      1320

AATCCCTTGT CATCTTCATT TCAGCAGGTC AGTGTTTTTT ATTCAGGTCC TCGTGATGAC      1380

ACAGAAGATA AAAACACCAA GTATTCTAAA AATTATCAAA TTGAATTTTA AGTTCAAAAG      1440

CATTCTTCCA TCACAGTCAA CAGAACCCCA AGACCTGAAG TTCCAAAGGC CTGTGGTGTT      1500

ACCACTATGC TATCTACATA TGTTACCTGC TTTTAACTAT TAAACGGAGC AGATGGATCA      1560

GAAGGTTAAT AGCTGATCAG ATCATGTCAG CTCATTAGCT TCAGTTTGTT TTACTGAGTG      1620

CTGTAACCAC TCAATCAGAA ACACACTGTT ACTTAATCTG AGTACATACT TGTATACATT      1680

AAACTTGGAA AAAGATAGAT GTGAAATGTA AAAGTGAGGT CAATCGTCAA ATGTGACACG      1740

ATATTTGGAT CTGTTTATCC TTCCAGGATC ACGGGGCGGG GAGAGCCTAT CCCAGCTACC      1800

ATAGTGCGAG AGGTCAGGTA CACCCTGGAC AGGTCAACAG CCTGTCACAG GGTTTACGCT      1860

CAGAGACAAG CAACCACGCC ACTTCGGCTT ATACCAGTAT TATTTCCTAA ATGTTGCCAA      1920

TAAAAAACAA AATCAGTAGA ATTTTAAGCA GTTTTCATTT TAATTTAACC TCATTTGAAG      1980

AAGAAGTCAG AGGTCCAAAG TATGGGAATA TTTATAATTC CAATGTTGTC AATTCAAATA      2040

ATGGCAATAA GAAACATAGT TTGAAATAGA AA                                    2072
```

(2) INFORMATION FOR SEQ ID NO:7:

(i) SEQUENCE CHARACTERISTICS:
        (A) LENGTH: 2075 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: HUMANIZED TILAPIA INSULIN NO:2

(xi) SEQUENCE DESCRIPTION: SEQ ID NO:7:

```
GTCCCCATAA TCGCACACAA GTCCCCACAA TGTAGGTGAA ATAGGTTCCA CGGAAACACG        60

TGGAACAGGG GGTGTGTCCA GGTGGTGCTG GTGGAGTATA AATGGAGAGA AGGCTCTTGG       120

TTCTGCCTCA CACAGAAAAG CTGCTCCTGC CCTTCATCTC AGAGTTACCT CCTCCTCTCT      180

GTCTGTGCAG GTGAGTGCTG GCTGTAGGTT TGGTTGTGAG GACAGTGACT GTGATGCTAA      240

CGTGAATGTG CTTTTGTGTT CAGCTCTTTT CCAGCATGGC AGCGCTCTGG CTCCAGGCCT      300

TCTCCCTGCT CGTCTTAATG ATGGTTTCGT GGCCGGGCTC CCAGGCCTTC GTGCAGCAGC      360

ACCTGTGCGG ATCCCACCTG GTGGAGGCCC TGTACCTGGT CTGTGGGGAG AGAGGCTTCT      420

TCTACACCCC CAAGACCAGA GATGTGGACC CTCTGCTTGG TGAGACCACC AACCACAAAC      480

AGAAACACTA GACAAACTAT TTGAGGGCAG CTTTTCTTTC TCTGAGTTCA CTTTAAATCA      540

GCTTTCATGT TGGAAACATG GTAATAGTAA TTTTCCATAT CTTTATGGAC CTACATGAT       600

TAGTTTACAT CTATTGCCAT TTGTCTCAAC ACCTGCATCA TATAATAGCG CTGATTTTGT      660

AACACTTTGT GTTAGAATTA GTAATTTATG TTCTAATAAT GTTTGATATG TATTCTTTAA      720

TATAAATGAC CAGAATTTTT AGATCTGAAC ATTCACCTGC TCTTCATCCC ATCAGGTTTC      780

CTCCCTCCAA AGGCAGGTGG TGCTGTGGTG CAAGGTGGTG AGAATGAAGT GACCTTCAAA      840

GACCAGATGG AAATGATGGT GAAGCGAGGC ATTGTGGAGC AATGCTGTAC CTCCATTTGT      900

TCCCTGTACC AGCTGGAGAA CTACTGCAAC TGAACTGCTC TGCTGGACTT TGTTTAGTCG      960

AGCCAGGCTC GGCTATTCAG GTCTGAGTCC CAGCCCCACC TCGCTCCCTG CTTCAGAGGA     1020

GAGCCACAGC TGTCCTCTCT CTGAAAACCA ACTGCTGTCA AATGAAGTGC TGAGAAATGG     1080
```

```
ATAAAATTAA TTTTCCAAGA AATAAAAATG CAAAATGTGA CAACGTGAGG CAAAAAAGTG      1140

TGTTCTTTTG TTGTGATGAA TTCAGTTAAT TGATTAAAGT GAAAACTCGA ACATGTTAGG      1200

TACCTGCTGC TATCCAGCAC AAACTGCTGA GCTTTCACTT TCCAAAGCTT TGTGTTTAGC      1260

TTATAGTGTC TCTGAACAGG ATATAAACAC ATCATGCACT CTGACATGAT GTCCTTTTCA      1320

AACAATCCCT TGTCATCTTC ATTTCAGCAG GTCAGTGTTT TTTATTCAGG TCCTCGTGAT      1380

GACACAGAAG ATAAAAACAC CAAGTATTCT AAAAATTATC AAATTGAATT TTAAGTTCAA      1440

AAGCATTCTT CCATCACAGT CAACAGAACC CCAAGACCTG AAGTTCCAAA GGCCTGTGGT      1500

GTTACCACTA TGCTATCTAC ATATGTTACC TGCTTTTAAC TATTAAACGG AGCAGATGGA      1560

TCAGAAGGTT AATAGCTGAT CAGATCATGT CAGCTCATTA GCTTCAGTTT GTTTTACTGA      1620

GTGCTGTAAC CACTCAATCA GAAACACACT CTTACTTAAT CTGAGTACAT ACTTGTATAC      1680

ATTAAACTTG GAAAAAGATA GATGTGAAAT GTAAAAGTGA GGTCAATCGT CAAATGTGAC      1740

ACGATATTTG GATCTGTTTA TCCTTCCAGG ATCACGGGGC GGGGAGAGCC TATCCCAGCT      1800

ACCATAGTGC GAGAGGTCAG GTACACCCTG GACAGGTCAA CAGCCTGTCA CAGGGTTTAC      1860

GCTCAGAGAC AAGCAACCAC GCCACTTCGG CTTATACCAG TATTATTTCC TAAATGTTGC      1920

CAATAAAAAA CAAAATCAGT AGAATTTTAA GCAGTTTTCA TTTTAATTTA ACCTCATTTG      1980

AAGAAGAAGT CAGAGGTCCA AAGTATGGGA ATATTTATAA TTCCAATGTT GTCAATTCAA      2040

ATAATGGCAA TAAGAAACAT AGTTTGAAAT AGAAT                                2075
```

TRANSGENIC FISH AND A METHOD OF HARVESTING ISLET CELLS THEREFROM

This application claims priority to PCT/CA96/00171, filed Mar. 22, 1996, which claims priority to U.S. application Ser. No. 08/417,866, filed Apr. 6, 1995, now abandoned.

TECHNICAL FIELD

This invention relates to transgenic fish containing a modified insulin gene which has been altered to secrete humanized insulin. This invention further relates to the xenotransplantation of transgenic islets in the treatment of diabetes and to an improved method for mass isolation of fish islets.

RELATED APPLICATIONS

Pursuant to 35 U.S.C. §§ 119(e) and 120, this application claims priority from WO 96/32087, filed Mar. 22, 1996, which claims priority from U.S. Patent Application 08/417,866, filed Apr. 6, 1995, now abandoned.

BACKGROUND OF THE INVENTION

Diabetes mellitus is a disease resulting in significant morbidity and mortality. The total annual direct and indirect costs of diabetes in the Unites States exceeds $90 billion dollars. Insulin-dependent diabetes mellitus (IDDM), because it occurs in a younger population than non-IDDM, accounts for a disproportionate percentage of these costs. Although the acute manifestations of IDDM can be controlled with daily insulin injections, most patients eventually develop sequelae such as blindness, nephropathy, neuropathy, microangiopathy, and cardiovascular disease. Substantial evidence suggests that meticulous control of glycemia will prevent or minimize these sequelae.

A more physiological method of treating diabetes would be pancreas or islet transplantation. Whole or segmental pancreas transplantation has been performed successfully in man and some preliminary evidence suggests that this technique will prevent the sequelae of diabetes in man. However, pancreas transplantation is not trivial surgery; it poses problems with drainage for exocrine secretions and requires a lifetime of immunosuppressive therapy. On the other hand, islet transplantation has certain theoretical advantages—particularly related to the ease of surgery, the absence of extraneous exocrine tissue, and the cryopreservability of isolated islets. More importantly, islets are more amenable to immunoalteration. Various methods have been developed to prolong allograft survival without continuous immunosuppression in rats and mice. The ability to transplant islets without continuous immunosuppression may eventually prove absolutely necessary in man because many immunosuppressive drugs are somewhat toxic to islets.

Recent improvements in the methods of mass islet isolation and several recent clinical reports suggest that islet transplantation is on the verge of becoming a feasible treatment for IDDM. However, several obstacles exist. First, islets comprise only 2% of the human pancreas; yields from human "islet isolation" procedures are extremely variable and several human donor pancreases are often required to generate sufficient islets for a single transplant. Second, islet allograft rejection has proven difficult to manage using conventional methods and, unfortunately, the majority of islet allografts are quickly lost. Third, there are insufficient human donor pancreases available to treat the vast numbers of type I diabetic patients. Therefore, it seems likely that widespread implementation of islet transplantation would require the development of clinical islet xenotransplantation.

In response to this eventuality, many biomedical corporations are spending millions of dollars developing and patenting "bio-artificial pancreas" technologies (i.e., microencapsulation or macroencapsulation of islet tissue). The underlying concept behind these approaches is that the islet tissue is protected from the immune system by a membrane with pore sizes small enough to prevent immunocytes and antibodies from damaging the graft yet large enough for insulin, oxygen, glucose, and nutrients to pass freely.

During the past few years, several clinical islet transplantation centers have devoted extensive effort to develop experimental islet xenotransplantation models using large animals as donors. Most of these studies have centered on porcine, bovine, canine, or non-human primate islets. However, the pancreata in these species, like the human pancreas, are fibrous and do not readily yield large quantities of intact, viable islet tissue. Moreover, generation of islet preparations from large animal donors is expensive and islet yields are variable.

We have developed a unique animal model for islet xenotransplantation utilizing tilapia, a teleost fish, as islet donors (1). The islet tissue in certain teleost fish, called principal islets or Brockmann bodies (BBs), is anatomically distinct from their pancreatic exocrine tissue and can be easily identified macroscopically. Expensive islet isolation procedures, such as required when procuring islet tissue from mammalian pancreases, are unnecessary. The BBs can be simply harvested with a scalpel and forceps. We have shown that tilapia islets transplanted into diabetic nude mice will produce long-term normoglycemia and a mammalian-like glucose tolerance curve (2).

Teleost fish insulin has been used to maintain human diabetics (1). However, it is likely that the immunogenicity of teleost insulin may prevent clinical application for BB xenotransplantation. On the other hand, the production of transgenic fish whose BBs produce humanized insulin may circumvent this problem. Transgenic fish which produce BBs that physiologically secrete humanized insulin, combined with improvements in bioartifical pancreas technology and encapsulation procedures, would eliminate the need for human pancreatic donors and islet isolation procedures.

Until recently, BBs were harvested manually by microdissection while visualized through a dissecting microscope inside a laminar flow hood (3). Although this was much easier and less expensive than the standard procedure of harvesting islets from rodents, it was a time consuming and tedious task. Although it was easy to harvest sufficient islets to perform xenografts in mice, this method was not well-suited to harvest large volumes of islet tissue as would be required for clinical use or large animal studies. Furthermore, microdissection allows us to collect less than 50% of the islet tissue per donor fish (i.e., those large BBs that are easily visible with the naked eye). Therefore, development of a more efficient method of harvesting BBs would be critical for the future application of fish islets as a donor source for clinical and experimental use. We have recently developed a mass-harvesting method (4).

To date, transgenic fish technology has been used to produce hardier fish that will grow rapidly and will tolerate adverse environments (5–6). Most of these efforts have been directed at insertion of growth hormone transgenes. Another approach has been to insert antifreeze genes from species that tolerate very cold waters (i.e., such as winter flounder)

into other species so that they will not only survive, but actually thrive in colder water. This approach permits aquaculture in more northerly regions and allows aquaculture stocks to grow year-round, rather than just during the summer growth season.

No previous transgenic fish studies have been directed at the insulin gene. In fish, insulin is primarily a growth hormone whereas, in mammalians, it is primarily a glucostatic hormone (7). Therefore, it is very likely that altering the expression and/or structure of the fish insulin gene may enhance growth. Consequently, a transgenic fish with altered fish insulin gene expression may demonstrate enhanced growth potential.

SUMMARY OF THE INVENTION

This invention relates to a humanized insulin gene capable of being expressed in a tropical fish islet cell wherein said gene comprises a coding sequence of an insulin gene under the control of regulatory sequences of the tropical fish insulin gene, wherein said humanized insulin gene encodes an insulin protein that is biologically active in humans.

The term "humanized insulin gene" as used herein means a modified fish insulin gene that contains a sufficient portion of the human insulin coding sequence to produce the humanized insulin product. The humanized insulin product should be biologically active when transplanted into a human and should contain sufficient human insulin sequences to avoid destruction of the humanized insulin product by the human immune system. In a preferred embodiment the humanized insulin gene should encode the alpha chain and at least the first 29 amino acids of the beta chain of human insulin.

The humanized or modified insulin gene further contains a sufficient portion of the regulatory sequences of the tropical fish insulin gene to allow expression of the humanized gene in tropical fish islet beta cells.

The present invention also relates to the preparation of a transgenic fish whose islet cells secrete humanized insulin.

This invention also relates to the islets of the transgenic fish and their use in xenotransplantation to treat diabetes.

In a preferred embodiment the tropical fish is a teleost fish such as tilapia.

This invention further relates to an improved method of harvesting principal islets comprising the steps of:

a) incubating the islets with collagenase for a period of time sufficient to release the islets from adipose and connective tissue; and b) separating the released islets from adipose and connective tissue.

This invention also relates to the use of the humanized insulin gene to promote growth in fish.

BRIEF DESCRIPTION OF THE DRAWINGS

FIG. 1—Amino acid sequence of the tilapia insulin hormone determined by automated Edman degradation. The amino acid sequence of the tilapia A chain and B chain is illustrated in SEQ. ID. No. 1 and 2, respectively.

FIG. 2—A comparison of the primary structure of the tilapia insulin with the human insulin. (-) represents sequence identity. The amino acid sequence of the A chain and B chain human insulin sequence is illustrated in SEQ. ID. No. 3 and 4, respectively.

FIG. 3—DNA and the corresponding amino acid sequence of tilapia insulin gene. The DNA sequence is also shown in SEQ. ID. No. 5.

FIG. 4—DNA and the corresponding amino acid sequence of a first humanized tilapia insulin gene. The DNA sequence is also shown in SEQ. ID. No. 6.

FIG. 5—DNA and the corresponding amino acid sequence of a second humanized tilapia insulin gene. The DNA sequence is also shown in SEQ. ID. No. 7.

DETAILED DESCRIPTION OF THE INVENTION

Selection of Appropriate Donor Species

When selecting a fish donor species for xenotransplantation one should consider the following seven criteria. First, the fish should be readily available locally or easily bred. Second, it should be large enough to work with easily. Third, the fish species should have one or more discrete BBs composed of relatively pure endocrine tissue. Fourth, the BBs must be able to tolerate culture at 37° C., the body temperature of the host, without undergoing necrosis, degranulation, or loss of function. Fifth, the species should maintain fasting plasma glucose levels in a mammalian range. Sixth, insulin secretion must be glucose dependent. And finally, the BBs must be able to maintain long-term normoglycemia after transplantation into diabetic nude mice.

In a preferred embodiment of the present invention, a warm water teleost fish is used as donor species. Phylogenetically, teleosts are a large and diverse infraclass of bony fish containing more than 30,000 species. Brockmann bodies (BBs) tend to occur only in "higher" teleosts; other teleosts tend to have disseminated islets. Tilapia (*Oreochromis nilotica*) and the giant *gorami* (*Osphronemus gorami*) are examples of tropical higher teleosts. Other tropical fish species having anatomically distinct islet tissue such as tambaqui (*Colossoma macropomum*) and Pacu (*Piractus mesopotamicus*) may also be used as donor species.

The primary structure of teleost insulins varies from that of man. Several teleost insulins have been purified and their amino acid sequences determined. All have an extra residue at the beginning of the B chain and are missing residue 30 at the end of the B chain; substitutions may occur at various other residues on both the A chain (e.g., 9 aa substitutions between human and cod insulin) and B chain (6 aa— human and cod). Most teleost fish insulins exhibit one-third to one-half the biological potency of human insulin (8).

Preparation of Humanized Insulin Gene

Tilapia insulin has been purified and sequenced (8) (FIG. 1). Tilapia insulin differs from human insulin by nine amino acids in the A-chain and eight amino-acids in the B-chain (FIG. 2).

Using an in vitro polymerase chain reaction (PCR) cloning strategy (Takara Shuzo Co. LTD) and nested degenerate primers based on conserved amino acids from human and several teleost fish insulins (9–11), the entire tilapia insulin gene has been cloned, including both 1 kb of 5' untranslated and 1.2 kb of 3' untranslated sequence (FIG. 3 and SEQ. ID. No. 5). The complete coding regions, including the leader sequence, B chain, C-peptide, and A chain have been sequenced. There is 100% identity between the deduced amino acid sequence and the protein sequence that was recently done by us using amino acid sequencing of purified tilapia insulin (FIG. 1). In comparison to human insulin, the tilapia A chain has 12/21 identical amino acids (57.1%) and five of the substituted amino acids are conserved changes. The B chain has 23/30 identical amino acids (76.7%) and three conserved changes when compared to the human protein. As expected, the C-peptide has little identity with the human C-peptide. The genomic structure of all known insulin genes contains an intron in the C chain. As expected, the tilapia insulin gene contains a 316 bp intron after the seventh amino acid in the C chain (phase 1). This intron has the proper GT/AG splicing donor/acceptor sequences. The 1 kb 5' upstream sequence should contain all the regulatory units so the gene is regulated (i.e. glucose responsive) in a tissue specific manner similar to its native counterpart.

Using site-directed mutagenesis and linker substitutions, the tilapia insulin gene was humanized so that it contains exons which code for human insulin while still maintaining all of the tilapia regulatory (non-coding) sequences. The substituted codons were devised so that they will code for the human insulin chains but will still use tilapia preference codons in order to get proper protein expression. The tilapia pre-insulin leader and the C chain were not altered. This construct will maintain all the similar recognition sites for the endopeptidases and, therefore, transgenic fish should technically process this modified protein as the native insulin. The first of the humanized tilapia genes lacks the human terminal threonine on the B chain (i.e., like tilapia) (FIG. 4 and SEQ. ID. No. 6); this will guarantee proper cleavage of the B-C chain. The second construct contains the terminal B chain threonine (FIG. 5 and SEQ. ID. No. 7).

Preparation of Transgenic Fish

To create transgenic fish, the humanized or modified gene is inserted into fertilized tilapia ova. First, the modified gene insert is removed from the plasmid DNA. The DNA is suspended in NT buffer (88 mM NaCl, 10 mM Tris-HCl pH 7.5) and $10^6$–$10^7$ copies are injected into each pronucleus (12). A linear fragment should increase the likelihood of integration and should also decrease extrachromosomal copies of the gene (12).

Unlike mice, which may produce 10–15 eggs at a time, fish may produce thousands of eggs at once. Tilapia are particularly prolific and are, in many ways, ideal for transgenic studies. Unlike many other teleost fish species which spawn once a year, female tilapia are ready to spawn every two weeks. Tilapia grow quickly and become sexually mature in five months.

Tilapia broodstock and offspring can be pit tagged to enable identification of individual fish by electronic scanning. Broodstock, a male and a female separated by a perforated plastic sheet, are kept in 20 gallon aquariums at 28° C. When the female becomes ripe, her eggs are stripped into a dry petri dish and the male's milt (semen) are stripped into a capillary tube. The tube's contents are mixed with the eggs and then water is added to the dish. After 2–3 minutes, the eggs are washed to remove excess sperm. Eggs are microinjected beginning within 5 minutes of fertilization. Fertilized eggs are maintained in water at 21° C., which slows down division, so that the fertilized eggs remain unicellular prior to injection. This technique has been reported to permit microinjection of tilapia eggs for 2.5 hours after fertilization (13).

Teleost fish eggs have micropyles, a single sperm-sized opening in the chorion. The micropyle diameter of a tilapia egg is 6 um. Micropyle injections are performed as described by Rahman and Maclean (13). Eggs are positioned with the micropyle readily visible and then immobilized in an egg holder designed by the inventors. With the aid of an operating microscope and a micromanipulator, the needle tip is advanced down the micropyle and 250 pl–2 nl of DNA solution injected using a "gene pusher". The needles, measuring 3–5 um at the end, are made from borosilicate glass tubes using an microelectrode puller. Following injection, the eggs are kept in plastic hatching funnels with a water flow rate of 0.75 1/minute until 10 days post-fertilization at which time the fry are transferred to an aquarium and allowed to grow (13).

Once introduced into tilapia by microinjection, the humanized tilapia insulin gene should contain enough tilapia sequences so that homologous recombination should occur in a miniscule percentage of fish. Homologous recombination is presently used in mice to disrupt genes (i.e., knockout experiments) to determine the in vivo function of the non-functioning disrupted gene. Tilapia fin clippings can then be screened using polymerase chain reaction (PCR) (14) using primers that incorporate the human sequences and do not give a product with the fish genome. Because of the great sensitivity of PCR, one can initially screen fin clippings in batches; one would then need to screen individual fish only when a positive batch is identified. Individual fish expressing the transgene would be pit tagged at 3 months of age so that they could be identified through their lives by electronic scanning.

Screening for Transgenic Fish

The objective of the breeding program is to develop a genetically stable production strain of transgenic tilapia for use in tissue transplantation. This line should have the following properties: (1) absence of humanized tilapia DNA sequences other than the insulin locus (extraneous humanized DNA), (2) homozygosity for the humanized insulin gene at the tilapia insulin locus, (3) genetic and developmental stability and uniformity, (4) good growth and survival characteristics, and (5) genetic identifiability for security against contamination and for protection of the proprietary interests of the developers.

Initial Screening Procedures:

The breeding program will be based in part on the screening with four PCR primers: primer (AT) tilapia sequence just upstream of the 1 kb leading strand of the insert, primer (BT) tilapia sequence in the leading strand outside the humanized coding region, primer (CH) humanized tilapia sequence in the insulin coding region, and primer (CT) tilapia sequence homologous to CH.

Homozygous Transgenic Founder Population:

The transgenic fish (generation GO) identified by initial screening for AT-CH PCR product will be heterozygotes at the insulin locus and may also contain extraneous humanized inserts elsewhere in the genome. These GO fish will be bred to as many wild-type individuals as possible, to produce a population containing 500% transgenic heterozygous offspring (G1) Fish containing one copy of the transgene will be selected by screening for the AT-CH PCR product. These heterozygous fish will then be mated amongst themselves to produce 25% homozygous transgenic fish in generation G2. The G2 homozygotes will be selected out from the 50% heterozygotes by simultaneous screening for AT-CH and AT-CT PCR products.

The resulting homozygous transgenic founder population will be expanded by random mating in the Marine Gene Probe Laboratory (MGPL) tilapia facility. We will then produce sufficient offspring so that we can purify and sequence the transgenic insulin to confirm its amino acid sequence.

Purified Transgenic Population:

Extraneous humanized inserts (other than at the insulin locus) in the founder population will be screened and culled by southern blotting restriction digests with a humanized tilapia insulin probe. This will be done in the GO and G1 generation. If the extraneous humanized inserts are rare, they will be selected out of the founder population by screening restriction digests with the humanized tilapia insulin probe. If they are very abundant, they will be diluted out by several generations of recurrent backcross selection to the non-transgenic base population in the MGPL, followed by another round of mating to re-establish homozygosity. The strategy will be to backcross the transgene to several strains of tilapia in the MGPL. When extraneous inserts have been removed, the purified transgenic population will be expanded by random mating.

The possibility that tissue from transgenic tilapia may ultimately be transplanted into humans sets rigid requirements for the stability and predictability of the material. The fish used for transplantation and associated support studies should be genetically uniform. It seems undesirable to aim for an isogenic transgenic strain that is homozygous at all background (non-insulin) loci, because of the generally poor fitness and low developmental stability of highly inbred fish. Instead, the goal should be an isogenic, first generation hybrid of homozygous line crosses. Such hybrids will be genetically identical, heterozygous at many background loci, but homozygous for the humanized tilapia insulin gene. Sib-mating rather than gynogenesis is a preferred procedure for production of homozygous lines. Multiple inbred parental lines will be developed as a security measure against loss of lines through inbreeding depression during sib-mating.

Transgenic Transplantation Strain:

Selection for fitness (growth and fecundity) in the inbred parental strains will be performed by within-family selection (15, 16). Selection will be initially on the strains themselves to reduce inbreeding depression and then secondarily on their performance in the isogenic transgenic hybrid. It is expected that selection for fitness will retard the approach of background loci towards homozygosity. This process will be controlled and monitored by extensive screening at microsatellite loci distributed throughout the genome. The final transgenic transplantation strain will be isogenic hybrid. The inbred parental lines will be sufficiently viable to create no risk of die-off during long term production of this strain.

Genetic Identification and Security:

If necessary (for example for security or proprietary reasons), the transgenic production strain may be identifiable as such, not only at the strain level but also at the chromosome level. This can be accomplished through the development of unique allele profiles at microsatellite loci on all chromosomes. If deemed necessary fish to be made available for transplantation can be made incapable of reproduction by hormonal sterilization.

Non-homologous Recombination:

As detailed above, we will attempt for homologous recombination. However, the humanized tilapia insulin gene will contain its "natural" promoter and other upstream regulatory sequences. Therefore, if integrated into another site (i.e. non-homologous recombination), it should still function. Islet cells from these transgenics would produce regulatable levels of both human and fish insulin.

Fish expressing both human and fish insulin genes may also be selected for production. Islets from such fish should still regulate blood sugar levels and, therefore, be useful as islet donors. Furthermore, fish expressing both genes (or multiple copies of the humanized gene) may demonstrate enhanced growth potential and, therefore, might prove valuable for aquaculture.

Harvesting BB's from Transgenic Fish

A new method of harvesting BBs using collagenase type II is described below. The procedure is much easier and less time consuming, especially when applied for mass isolation; it has more than doubled the yield of islet tissue per fish and, therefore, decreased the need for donor fish by >50%. Histologically, BB preparations harvested in this manner are cleaner than BB preparations acquired by microdissection. The inventors have previously transplanted the BBs from tilapia isolated by this new method into athymic nude mice as well as into euthymic BALB/c mice and compared the results with those of using fish islets harvested by the standard microdissection method. The results indicated that this new isolation method does not alter either long-term function after transplantation in nude mice or mean graft survival time after transplantation in euthymic mice (4).

Donor fish are housed at 28° C. and fasted prior to sacrifice. Donor fish are anesthetized by placing them in a bucket of water containing 2-phenozyethanol (1 ml/L) or ethyl p-aminobenzoate (benzocaine) (200 mg/L); the fish are then weighed and given an identifying number. Next, each fish is placed on its left side in a dissecting tray. The donor fish is then killed by cutting the cervical spinal cord with a scalpel. Next, the peritoneal cavity is widely exposed by cutting along the ventral surface from the anus to the pericardial cavity; this cut is extended dorsally caudal to the right operculum (gill flap) and then caudally along the dorsal aspect of the peritoneal cavity to the anus. Finally, the triangular flap of musculointegumentary tissue bounded by these three cuts is removed (4). The "EBB region" adjacent to the bile duct is identified in situ (4), excised, and placed into a petri dish (4) containing Hanks balanced salt solution (HBSS) containing 27 mM Hepes, 200 U/ml penicillin, and 200 ug/ml streptomycin sulfate (Gibco, Grand Island, N.Y.); dish is labelled with the fish identifying number. The dish is then placed in a laminar flow hood and held until any additional donor fish have been processed through these steps.

Microscopically, these BB regions are composed of adipose tissue, blood vessels, nerves, bile ducts, and approximately 15 BBs (4). The BB regions are collected and kept in cold Hanks balanced salt solution (HBSS) containing 27 M HEPES, 200 U/ml penicillin, and 200 ug/ml streptomycin sulfate (Gibco, Grand Island, N.Y.). After collecting the required number of BB regions, they are rinsed and placed in a 50 ml plastic centrifuge tube containing 37° C. prewarmed collagenase solution (2 regions/ml). The collagenase solution is prepared by dissolving collagenase type II (Sigma C-6885, St. Louis, Mo.) in HBSS at a concentration of 3 mg/ml. Next, each tube containing BB regions and collegenase solution is placed in a 37° C. shaker/water bath. Digestions are carried out for approximately 15±5 minutes. The optimal digestion time is judged visually by periodically stopping the digestion and holding the tube against a light. Digestion is stopped when most of the small and moderate-sized BBs were clearly liberated while the largest BBs are still weakly attached to a few thread-like structures. The digestion is stopped by pouring cold HBSS into each tube. The tubes are centrifuged for 1 minute at 1000 RPM and the supernatant containing a layer of free adipocytes and the diluted collagenase is discarded. The pellet is washed twice with cold HBSS. The digested tissue is then resuspended in HBSS and placed into 100 mm plastic culture dishes. Under the dissecting microscope (10× magnification) or with the naked eye plus good illumination, the released BBs can be easily identified from the residual debris composed of vessels, bile ducts, and connective tissue. The BBs appear spherical and whitish; they are less translucent than the connective tissue (4). They are then handpicked using a siliconized pipette. Usually, each donor fish has one or two large BBs and 10–15 small or intermediate-sized BBs; the size of the BBs ranged from 0.3–5mm in maximum dimension (4). The largest BBs often are intimately associated with a large caliber blood vessel and this is usually still weakly attached after digestion (4); however, this is easily separated with the help of microvascular scissors and jeweller's forceps. All collected BBs are then transferred into CMRL-1066 culture medium (Gibco, Grand Island, N.Y.) plus lot calf serum, 2.5 mg/ml D-glucose, 100 U/ml penicillin, and 100 ug/ml streptomycin sulfate. The larger BBs are divided with microscissors to achieve a uniform size (<0.5 mm in maximum dimension). Then all BB fragments are cultured overnight free-floating at 37° C. in 95% air/5% $CO_2$. BB fragments are cultured overnight before transplantation to allow insulin to leak out of any damaged cells and to permit exocrine tissue attached to the BB fragments to degenerate prior to transplantation. Once all petri dishes are in the incubator, plasma glucose levels for each donor fish are determined and recorded by donor fish identifying number. After overnight culture, the BB fragments are ready for transplantation.

Functional Studies

Prior to clinical use, the functional characteristics of the transgenic islets need to be characterized. This is to be done in vitro and in vivo. As a first step, the amino acid sequence of the secreted insulin from the transgenic islets is determined to confirm that it is humanized. The kinetics of tilapia insulin secretion by non-transgenic tilapia islets as well as its secretagogues are determined in vitro and compared to secretion studies using transgenic islets and a radioimmunoassay for human insulin. Because the structure of piscine insulin differs from human, porcine, bovine, and rat insulin amino acids, most antibodies produced against insulin of these species do not crossreact with an affinity sufficient for radioimmunoassay. Although a few antibodies have been raised against teleost fish insulin (17–21), the insulin of one teleost species often differs from that of other teleost species. Therefore, an antibody to purified tilapia insulin (8) has been raised to permit insulin measurement by standard RIA methodology.

Further, the comparative effects of tilapia, humanized tilapia, and human insulin on mammalian muscles cells, one of the primary targets of insulin, will be studied. IDDM adversely affects glucose transport, glycogen synthesis, glucose oxidation, and glucose transporter GLUT-4 translocation and/or activity; these problems are normalized by appropriate insulin treatment. Therefore, the acute and chronic effects of treatment with humanized tilapia insulin on glucose transport, glucose metabolism (glycogenesis, glycolysis, and oxidation), insulin binding, and GLUT-4 translocation will be examined. In addition, some of these chronic studies will be performed on streptozotocin-diabetic athymic nude mice which have been made normoglycemic with BB grafts.

Transgenic islets will function appropriately in a mammalian recipient. This is done as in the inventors previous studies transplanting non-transgenic fish islets into nude mice (1,2). Diabetes should be induced in recipient mice at least one week prior to transplantation with a single intravenous injection of streptozotocin (175–200 mg/kg); all recipient mice should have at least two successive non-fasting plasma glucose measurements between 350 and 500 mg/dl. For all mouse strains the inventors have tested, the optimal volume of tilapia BB fragments to insure normoglycemia and to minimize the probability of hypoglycemia immediately post transplantation is about 0.0025 kg of donor fish body weight/gm of mouse weight (eg., a 24 gm mouse would require about 0.6 kg of donor tilapia). The total donor fish body weight can generally be provided by one large fish or multiple small fish. Tilapia weighing between 200 and 800 gms each are usually used as BB donors. Interestingly, donor fish body weight does not seem to correlate closely with BB weight, consequently total donor fish weight seems to be the better method for quantifying the amount of tissue required for transplantation into a particular recipient mouse.

At least 30 minutes before transplantation, BB fragments are removed from the incubator, switched into CMRL media containing 4.0 mg/ml D-glucose, and then returned to the incubator for 30 minutes. This steps further degranulates the islets and serves to protect the recipient from acute hypoglycemia during the first 24–48 hours after transplantation (i.e, when insulin is most likely to leak out of any dead or dying cells). After this 30 minute incubation period, BB fragments are placed in complete media containing 2.5 mg/ml D-glucose and then returned to the incubator until the time they are transplanted. Immediately prior to transplantation, the BB fragments are washed in incomplete media (i.e., without fetal calf serum).

The diabetic nude mouse recipient is anesthetized with an i.p. injection of 50–55 mg/kg sodium pentobarbitol, placed on its right side and secured. The left side is shaved and then cleansed with an iodine antiseptic solution followed by alcohol. The left kidney is palpated and then delivered through a 0.75 cm subcostal incision at the costovertebral angle. The externalized kidney is secured and moistened with Hepes-HBSS. While visualized through a dissecting microscope, the renal capsule is gently lifted with jeweller's forceps and a 0.2 cm incision is made with the cutting edge of a 25 gauge needle. A "hockey stick-shaped" glass microspatula is used to separate the capsule from the surface of the kidney—thus creating a space into which the BB tissue may be transplanted. Great care must be exercised to prevent tearing of the renal capsule with the microspatula.

BB fragments are placed beneath the kidney capsule by gently lifting the capsule with curved jeweller's forceps and then pushing each fragment under the capsule with the curved glass microspatula. The surface of the kidney should be frequently moistened with hepes-HBSS during this process. Once all of the BB fragments are under the kidney capsule, they should be distributed evenly so that large matted masses of BB tissue are avoided. The incision in the renal capsule is then sealed using a fine tip, low-temperature ophthalmic cautery (Xomed-Treace, Jacksonville, Fla.). The kidney is then returned to its normal position and the muscular layer and the skin are closed individually with 5-0 silk suture (2, 22).

Transplant Assessment a. In vivo craft function

Mice generally become normoglycemic (<200 mg/dl) several hours post-transplant. Recipient mice should be observed occasionally in the post-operative period for signs of hypoglycemia. During the first 24–48 hours post transplantation, insulin release is poorly regulated and mice may fall victim to hypoglycemia. Hypoglycemic mice should be treated immediately with i.p. glucose. If sufficient volume of BB tissue has been transplanted, mice should remain normoglycemic until rejection. Mean non-fasted plasma glucose levels after transplantation of tilapia BB fragments into nude mice are in the range of 70–100 mg/dl (2); however, mean plasma glucose levels tend to be somewhat lower during the first week after transplantation. BB grafts function physiologically in nude mice; long-term recipient mice have relatively normal glucose tolerance curves (2). It is of interest that mean fasting plasma glucose levels (72 mg/dl) in long-term recipient mice are nearly identical to those of the donor fish (75 mg/dl) (2). The inventors have found that, if non-fasting plasma glucose levels fluctuate widely, it is likely that insufficient BB tissue was transplanted (23).

b. Histology

Histological assessment is required when each recipient mouse is sacrificed. First of all, the recipient's native pancreas should be examined histologically for evidence of Beta cell regeneration; this is accomplished by staining histologic sections for insulin with aldehyde fuchsin (24) or immunoperoxidase.

Next, each left kidney should be examined for graft viability and the degree of Beta cell granulation. Beta cell granulation can be examined by immunoperoxidase staining using the inventors, antibody to tilapia insulin. Sections of the graft-bearing kidney should also be stained with hematoxylin and eosin.

c. Single cell preparations

There may be some advantage to converting the BB fragments to single cell suspensions. This is associated with an additional advantage in that single cells and small cell agglomerates display a much higher surface area to volume ratio than whole BBs or BB fragments and, therefore, are less susceptible to limitations in the diffusion of oxygen and nutrients (25).

BBs can be easily dispersed into single cells. BBs are placed in a 15 cc plastic conical centrifuge tube and washed twice with calcium-magnesium-free HBSS. This is aspirated and the BB are resuspended in 7 ml of versene (Gibco #670–5040AG, Grand Island, N.Y.) at room temperature for seven minutes. The BBs are sedimented and the supernatant removed. Next, 4 ml of a trypsin solution (Sigma #T-0646, St. Louis, Mo.; 1 mg/ml in calcium-magnesium-free HBSS filtered through a 0.22 um syringe filter) is added to the tube and the tube is then placed in a 37° C. water bath inside a laminar flow hood; the trypsin/BB solution is then gently pipetted up and down constantly. After two minutes, the larger fragments are allowed to sink to the bottom and the supernatant containing free islet cells is removed and immediately transferred to a tube containing complete tissue culture media which is then placed on ice. An additional 4 ml of the trypsin solution is added to the pellet and this process is repeated three times. Each time the supernatant is pooled and diluted with complete media. Finally, the tube containing the supernatant is centrifuged at 600 g for 5 minutes at 4° C. The supernatant is removed and the cells are resuspended in complete tissue culture media and counted. Viability, as assessed by trypan blue exclusion, is about 95%. Compared to dispersed rodent or human islet cells, dispersed BB cells have less tendency to reaggregate into clumps or chains of cells after overnight culture although some reaggregation will occur as illustrated in FIG. 10. Although single cell suspensions immobilized in plasma clots will produce normoglycemia when transplanted under the renal capsules of diabetic nude mice, data suggests that single cell preparations do not function in vivo quite as well as BB fragments—probably because cell-cell communications are diminished (26).

As an alternative to single cell methods, mammalian islet-sized BBs ("micro-BBs") can be produced with a Cellector Tissue Sieve (Bellco Glass, Vineland, N.J.) simply by pushing BE fragments sequentially through a sterile stainless steel #60 mesh (opening size 230 um) filter and then through a sterile #80 mesh (opening size 190 um) filter. Both filters should be carefully washed with excess media. All filtrates should be collected in plastic petri dishes and cultured overnight. Because BBs are composed of almost pure endocrine cells and have minimal connective tissue stroma, very little tissue should remain on the filters after several washes. Although the "micro-BBs" initially appear ragged when the dishes are examined with an inverted microscope, they "round up" nicely after overnight culture and appear remarkably similar to cultured mammalian islets. After culture, "micro-BBs" can be hand-picked with a Pasteur pipette and counted while visualized through a dissecting microscope housed within a laminar flow work station. It seems likely that "micro-BBs" may function better than single cells because some cell-cell communication remains intact. Unlike BB fragments, "micro-BBs" are small enough that they can be transplanted into sites other than under the kidney capsule. Alternatively, the BBs can simply be teased apart and then cultured which will produce similar mammalian islet-sized BBs. We have previously shown that micro-BBs prepared in this fashion from non-transgenic tilapia can be successfully transplanted into the testes of diabetic nude mice and will produce long-term normoglycemia.

Transplantation Into Humans

BBs from transgenic fish of the present invention, once characterized, can be harvested, encapsulated, and surgically transplanted into diabetic patients. The BBs can be encapsulated according to known techniques in the art for encapsulating islet cells (27–29). We have previously shown that macroencapsulated BBs from non-transgenic tilapia will provide long-term normoglycenia and mammalian-like glucose tolerance profiles after intraperitoneal transplantation in mice (30).

One problem that has plagued investigators working with the various artificial pancreas technologies is that much of initial islet volume is lost after encapsulation because of central necrosis secondary to hypoxia in the centre of the islets. It is very likely that piscine islet tissue would be superior to mammalian islet tissue for encapsulation because fish tissues, including islets, can tolerate lower oxygen tensions (31). Even if glucose-stimulated insulin secretion. by the transgenic fish islets proved to be somewhat less efficient or slightly slower than that of human islets, they still might prove exceedingly useful for artificial pancreases with a large number of fish islets and a much smaller number of human islets; conceivably the fish islets could provide the bulk of the insulin production and the human islets could "fine tune" the insulin response just as short-acting and long-acting insulins are now mixed to optimize insulin therapy in diabetics.

Transgenic fish islets described herein represent a nearly unlimited supply of human insulin-producing islet tissue that would not require expensive enzymatic islet isolation procedures for procurement. The utility of these islets is likely to be further increased in that we have shown that tilapia BBs can be cryopreserved in liquid nitrogen (using standard technique developed for cryopreserving mammalian islets), thawed, and then transplanted into diabetic nude mice confirming islet function. This would facilitate shipping and long-term storage of the transgenic islets.

Other Applications of the Invention

As described in detail above, the transgenic fish of the present invention are useful in providing large amounts of humanized insulin for the treatment of diabetes. This occurs through the homologous recombination of the humanized tilapia insulin gene. However, if non-homologous recombination occurs, the transgenic fish may express both human and fish insulin genes. Such fish may be useful in aquaculture as fish expressing both genes (or multiple copies of the human gene) may demonstrate enhanced growth potential.

One skilled in the art can readily appreciate that various modifications can be made to the invention without departing from the scope and spirit of invention. Modifications intended to be within the scope of the invention include modifications or substitutions to the sequence of the humanized insulin gene which do not substantially affect the biological activity or immunogenicity of the insulin product in humans.

REFERENCES

1. Wright, J R Jr: Experimental transplantation using principal islets of teleost fish (Brockmann bodies). In *Pancreatic Islet Cell Transplantation: 1892–1992—One Century of Transplantation for diabetes,* edited by C. Ricordi, R.G. Landes Co., Austin, 1992, p. 336–351.
2. Wright J R Jr., Polvi S and Maclean H: Experimental transplantation using principal islets of teleost fish (Brockmann bodies) : Long-term function of tilapia islet tissue in diabetic nude mice. Diabetes 41:1528–32. 1992.
3. Wright J R Jr. Preparation of Fish Islets (Brockmann bodies) In: Lanza R P; W L Chick, eds. *Pancreatic Islet Transplantation genes* Vol. 1. *Procurement of Pancreatic Islets.* Austin: RG Landes co.; (1994:123–32).
4. Yang H and Wright J R Jr: A method for mass harvesting islets (Brockmann bodies) from teleost fish. Cell transplant. 4:621–8, 1995.
5. Hackett P B: The molecular biology of transgenic fish. In: *Biochemistry and molecular Biology of Fishes,* 2. Hochachka P and Mommesen T (eds.) Amsterdam: Elsevier, 1993.
6. Hew C L and Fletcher G, eds.: *Transgenic Fish.* New Jersey: World Scientific, 1992.
7. Mommesen T P and Plisetskaya E M: Insulin in fishes and agnathans: history, structure, and metabolic regulation. Rev. Aquatic Sci. 4:225–59, 1991.
8. Nguyen T M, Wright J R Jr Nielson P F, and Conlon J M: Characterization of the pancreatic hormones from the Brockmann body of the tilapia-implications for islet xenograft studies. Comp. Biochem. and Physiol. 111C:33–44, 1995.
9. Hobart P M, Shen L -P, Crawford R. Pictet R L and Ruttner W J: Comparison of the nucleic acid sequence of anglerfish and mammalian insulin mRNA's from cloned CDNA's. Science 210: 1360–3, 1980.
10. Chan S J, Cao Q -P, Nagamatsu S, and Steiner D F: Insulin and insulin-like growth factor genes in fishes and other primitive chordates. In: *Biochemistry and molecular Biology of Fishes,* 2, Hochachka P. and Mommesen T. (eds.) Amsterdam: Elsevier, 1993, pp. 407–17.
11. Steiner D F: Structure and evolution of the insulin gene. Ann. Rev. Genet. 19: 463–84, 1985.
12. Penman D J, Beeching A G, Penn S, and MacLean N: Factors affecting survival and integration following microinjection of novel DNA into rainbow trout eggs. Aquaculture 85: 35–50, 1990.
13. Rahman M A and Maclean N: Production of transgenic tilapia (*Oreochromis niloticus*) by one-cell-stage microinjection. Aquaculture 105: 219–32, 1992.
14. Saiki R K, Gelfand D H, Stoffel S, Scharf S J, Higuchi R, Horn G T, Mullis K B, and Erlich H A: Primer-directed enzymatic amplification of DNA with a thermostable DNA polymerase. Science 239: 487–91, 1988.
15. Uraiwan S and Doyle R W: Replicate variance and the choice of selection procedure for tilapia (*Oreochromis nilotic*) stock improvement in Thailand. Aquaculture 57: 93–8, 1986.
16. Doyle R W and Herbinger C: The use of DNA fingerprinting for high-intensity, with-in family selection of fish breeding. 5th World Congress, Genetics Applied to Livestock Production. Guelph, Ontario, Canada, pp. 364–371.
17. Furuchi M. Nakamura Y. Yone Y. A radioimmunoassay method for determination of fish plasma insulin. Bull Jap Soc. Sci Fish 1980; 46:1177–81.
18. Patent T N, Foa P P. Radioimmunoassay of insulin in fishes: Experiments in vivo and in vitro. Gen Comp Endocrinol 1971: 16:41–6.
19. Plisetskaya E M, Leibush B N. Radioimmunological determination of insulin in lower vetebrates. Zh Evol Biokhim Fiziol 1974; 10:623–5.
20. Thorpe A. Ince B W. Plasma insulin levels in teleosts determined by a charcoal-separation radioimmunoassay technique. Gen Comp Endocrinol 1976: 30:332–9.
21. Tilzey J F, Waights V, Holmes R. The development of a homologous teleost insulin radioimmunoassay and its use in the study of adrenaline on insulin secretion from isolated pancreatic islet tissue of the rainbow trout. *Salmo gairdnerii* (R.). Comp Biochem Physiol. 1985: 81A–821–5.
22. Wright J R Jr, Kearns Il, Polvi S et al. Experimental xenotransplantation using principal islets of teleost fish (Brockmann bodies) : Graft survival in selected strains of inbred mice. Transplant Proc. 1994; 26:770.
23. Wright J R Jr, Polvi S, Schrezenmeir J., Al-Abdullah I. Longterm function of teleost fish principal islets (Brockmann bodies) after transplantation under the renal capsule in diabetic nude mice. Transplant Proc. 1992: 24:3029–30.
24. Culling C F A, Allison R T, Barr W T, Aldehyde fuchsin (Halmi, 1952), In: Cellular Pathology Technique 4th ed., London: Buttherworths, 1985: 47808.
25. Schrezenmeir J, Laue Ch, Sternheim E T et al., Long-term function of single-cell preparations of piscine principal islets in hollow fibers. Transplant Proc. 1992; 24:2941–5.
26. Pipeleers D, In't Veld P, Maes E, and Van de Winkel M: Glucose-induced insulin release depends on functional cooperation between islet cells. Proc. Natl. Acad. Sci. USA 79: 7322–5, 1982.
27. Iwata H, Kobayashi K, Takagi T, Oka T, Yang H, and Amemiya H: Feasibility of agarose microbeads with xenogeneic islets as a bioartifical pancreas. J. Biomed. Mater, Res. 28: 1003–11, 1994.
28. Iwata H, Takagi T, Kobayashi K, Oka T, Tsuji T, and Ito F: Strategy for developing microbeads applicable to islet xenotransplantation into a spontaneous diabetic NOD mouse. J. Biomed. Materials Res, 28: 1201–7, 1994.
29. Lanza R P, Ecker D, Kuntreiber W H, Staruk J E, Marsh J, and Chick W L: A simple method for transplantating discordant islets into rats using alginate gel spheres. Transplantation 59:1485–9, 1995.
30. Yang H & Wright J R Jr: Long-term function of fish islet xenografts in mice by alginate macroencapsulation. Abstract submitted for International Congress of the Transplantation Society, Barcelona.
31. Schrezenmeir J, Kirchgessner H, Gero L, Kunz L A, Beyer J, and Mueller-Klieser W: Effect of microencapsulation on oxygen distribution in islets organs. Transplantation 57: 1308–14, 1994.

We claim:

1. A method for harvesting principal islets from fish, said method comprising:
   a) incubating islet-containing tissue obtained from fish, wherein said islet-containing tissue comprises adipose tissue and connective tissue, with collagenase type II for a period of time sufficient to release the islets from adipose and connective tissue; and
   b) separating the released islets from said adipose and connective tissue.

2. The method according to claim 1 wherein, in step a), the islet-containing tissue is incubated with the collagenase at 37° C. for about 10 to about 20 minutes.

* * * * *